United States Patent [19]

Furukawa

[11] Patent Number: 4,850,975
[45] Date of Patent: Jul. 25, 1989

[54] CATHETER INTRODUCER FOR ANGIOGRAPHY

[76] Inventor: Yuichi Furukawa, 112, 2-Chome, Kamihama-Cho, Tsu-Shi, Mie-Ken, Japan

[21] Appl. No.: 168,805

[22] Filed: Mar. 16, 1988

[30] Foreign Application Priority Data

Mar. 27, 1987 [JP] Japan .................................. 62-75552

[51] Int. Cl.$^4$ ............................................. A61M 5/00
[52] U.S. Cl. ....................................... 604/170; 604/53; 128/343; 128/658
[58] Field of Search ...................................... 604/51–53, 604/168–170, 280–283, 104; 128/343, 658

[56] References Cited

U.S. PATENT DOCUMENTS

| | | | |
|---|---|---|---|
| 4,411,655 | 10/1983 | Schreck | 604/104 |
| 4,451,256 | 5/1984 | Weikl et al. | 604/164 |
| 4,498,902 | 2/1985 | Ash et al. | 604/164 |
| 4,610,674 | 9/1986 | Suzuki et al. | 604/167 X |
| 4,619,644 | 10/1986 | Scott | 604/53 |
| 4,629,450 | 12/1986 | Suzuki et al. | 604/104 |
| 4,699,611 | 10/1987 | Bowden | 604/105 X |

FOREIGN PATENT DOCUMENTS

61-71065 4/1986 Japan .

Primary Examiner—Dalton L. Truluck
Attorney, Agent, or Firm—Armstrong, Nikaido, Marmelstein, Kubovcik & Murray

[57] ABSTRACT

A catheter introducer for angiography is disclosed which comprises a sheath for inserting and guiding a catheter into a puncture hole in a blood vessel, and a dilator removably inserted through the sheath for receiving an introduction guide wire for the catheter. A front end of the dilator is provided with a forwardly descending conical taper surface for smoothly expanding the puncture hole. A rear end of the dilator is formed with a hub which extends therefrom for preventing the slip-off of the sheath. The sheath has a hollow hub which extends from the rear end thereof. The hub is connected for communication to a medical liquid injecting tube which is equipped with an on-off valve for injecting a heparin-containing physiological salin solution or other medical liquids for preventing blood coagulation. The outer diameter of a portion of the dilator subsequent to a forwardly descending taper surface is greater than the inner diameter of the sheath. A slit for contracting the outer diameter is cut in the dilator to extend longitudinally along the dilator in the form of a line segment of a given length such that an opening front end of the dilator is positioned on the forwardly descending taper surface and an opening rear end of the dilator is limited from reaching a sheath slip-off preventing hub of the dilator. The dilator is inserted through the sheath while being forcibly contracted to cause the slit to close. The dilator is intimately contacted with the inner wall surface of the sheath.

3 Claims, 8 Drawing Sheets

Fig.10(III)

Fig.10(VII)

CATHETER INTRODUCER FOR ANGIOGRAPHY

BACKGROUND OF THE INVENTION

In angiographic tests based on DSA (digital subtraction angiography) and other computer images, the frequency of use of the trans-brachial artery catheterization technique is still low at present, the trans-femoral artery catheterization technique being frequently used. The reason seems to be the lack of the safety of catheter manipulation and the lack of a selective or superselective catheter manipulating technique directed to the systemic arteries.

The trans-brachial artery catheterization technique, however, has the advantage that hemostasis subsequent to a test can be effected in the state which allows the patient to walk, a fact which means that this catheterization technique is also applicable to outpatients. Thus, if said selective or superselective catheter manipulating technique is developed and its safety is confirmed, there is no doubt that such technique will play a major role in the advancement of angiographic testing.

In this connection, it is known that generally in the trans-brachial artery catheterization technique, since the catheter has to be inserted into a puncture hole formed in the thin brachial artery, a thrombus or occlusion tends to form in the brachial artery subsequently to a test. To prevent this, it is necessary to use a catheter which is as thin as possible, having a diameter less than the inner diameter of the brachial artery while ensuring blood flow even during insertion of the catheter.

Increasing blood flow in the brachial artery also serves to prevent formation of a thrombus or occlusion. In this connection, it is to be pointed out that in more than 250 cases in which I performed the technique of having each patient hold an athletic appliance in his hand and firmly squeeze it with time during insertion and manipulation of a catheter, formation of a thrombus or occlusion was not found.

Even if a thin catheter is used, frequent occurrence of excessive direct stimulus to the brachial artery or damage to the artery wall as well as bleeding during insertion or manipulation of the catheter leads to thrombus formation or occlusion; thus, these inducers must be removed before the safety of the trans-brachial artery catheterization technique can be enhanced.

Inasmuch as the trans-brachial artery catheterization technique is based on the principle of inserting the catheter into the artery and remote manipulating the catheter, it is extremely difficult both theoretically and practically to eliminate direct stimulus to the brachial artery wall or damage to the artery wall during insertion and manipulation of the catheter. This can also be said from the nature of the manipulation involved in the aforesaid catheterization technique wherein a catheter which is thinner and longer than in the case of the trans-femoral artery catheterization technique is required and has to be remote-manipulated safely and reliably by a single person.

However, it is theoretically possible to reduce, if not eliminate, the same. That is, there are two types of causes of direct stimulus to the artery wall during manipulation of the catheter. A first type is due to friction of contact between the catheter and the artery wall in a hole in the front wall region of the artery in which the catheter is inserted, and a second type is due to contact between the inner wall surface of the brachial artery and the catheter during manipulation of the catheter.

In reducing direct stimulus due to the first type of cause, methodologically it is contemplated either to increase the opening size of the hole in the front wall region of the artery beyond the outer diameter of the catheter or to use a separate catheter introducer to avoid friction of contact between the catheter and the artery wall. The method based on increasing the opening size of the hole in the front wall region of the artery beyond the outer diameter of the catheter has a high degree of danger of bleeding; therefore, in performing said trans-brachial artery catheterization technique, I make it a rule to use a catheter introducer as well.

As for reducing direct stimulus due to the second type of cause, I was able to attain this reduction by performing said trans-brachial artery catheterization technique while simultaneously using an introduction guide wire (a product from Terumo Kabushiki Kaisha: trade name, Radiofocus M) which is superior in pliability associated with remote manipulation of the catheter and which does not form a fixed bend when subjected to an external force. The simultaneous use of this guide wire enables the catheter to transmit torque in its bent state and to rotate while sliding along the inner wall surface of the brachial artery, with the result that the state of the catheter pressing the artery wall is reduced and so is direct stimulus.

While the role which the catheter introducer is expected to play is as described above, conventional articles, now commercially available, have the following problems in applying them to the trans-brachial artery catheterization technique.

A catheter introducer comprises a sheath for introducing or guiding the catheter into a puncture hole in the artery, and a dilator removably inserted through said sheath to receive an introduction guide wire for the catheter. Thus, the inner diameter of the sheath is 1 French size greater than the outer diameter of the catheter, and even if a thin catheter is purposely used, the result is the same as if a thick catheter, which is 1 French size greater, were used, thus forming a cause of impediment to blood flow in the brachial artery.

Moreover, said sheath does not have a mechanism which brings it in intimate contact with the dilator inserted therethrough. The outer diameter of the dilator is smaller than the inner diameter of the sheath, and the two parts are merely fitted together on the basis of a construction in which the two sizes do not produce a varying elastic action; therefore, an air gap, even though small, is inevitably produced in the fitting surface.

As a result, even if the sheath is thin-walled, the front end step portion of the sheath relative to the dilator forms a cause of damaging the artery wall when the introducer is inserted into the artery. The reason is that the thin wall of the sheath causes the front end step portion to crack and turn back as if burred.

SUMMARY OF THE INVENTION

The present invention, intended to solve the problems described above, is characterized in that a dilator having an outer diameter greater than the inner diameter of a sheath can be inserted through the sheath in intimately fitted relation. The use of such catheter introducer effectively reduces said thrombus formation or occlusion in the artery and greatly enhances the diagnostic value of angiographic tests not only in the trans-femoral but also trans-brachial artery catheterization techniques.

That is, a first object of the invention is to provide an arrangement wherein while the outer diameter of the dilator is made greater than the inner diameter of the sheath, the dilator is formed with a slit of given length extending longitudinally of the dilator, whereby through the closing action of the slit developed during insertion of the dilator through the sheath, the outer diameter of the dilator is forcibly contractively deformed, producing a restoring elastic force for spontaneous expansive deformation, said restoring elastic pressure acting to intimately contact the dilator with the opening inner wall surface of the sheath, wherein the wall thickness of said sheath is minimized while preventing an air gap from being produced in the fitting surface between the sheath and the dilator and also preventing the front end step portion of the sheath from being burred to ensure easy and safe insertion into the artery.

A second object is to provide an arrangement wherein the reduction of the wall thickness of the sheath, which helps to thin the introducer itself, is utilized to reduce impediment to blood flow in the artery, to reduce the later expansion of a puncture hole in the artery and to reduce friction of contact and to provide easy and perfect hemostasis.

A third object is to provide an arrangement wherein in making the outer diameter of the dilator greater than the inner diameter of the sheath, the front end of the dilator or a portion adjacent said front end is formed with a forwardly descending conical taper surface to thereby more smoothly increase the outer diameter while positioning the opening front end of said slit on said conical taper surface, so that when the dilator is inserted into the sheath and advanced therein, the slit is subjected to a force from the conical taper surface and thereby urged to gradually close, whereby the dilator can be contractively deformed extremely smoothly and the dilator can be easily inserted through the sheath.

A fourth object is to provide an arrangement wherein the state of intimate fitting between the dilator and the sheath is established by a restoring elastic pressure accompanying the contractive deformation of the dilator, thereby making it possible to effectively accommodate fitting dimensional errors produced during manufacture. Other objects of the invention, together with the concrete construction of the invention, will become apparent from the following description of embodiments.

BRIEF DESCRIPTION OF THE DRAWINGS

FIGS. 10 (I) through 10 (VII) are explanatory views showing the steps of insertion of a catheter using an introducer;

DESCRIPTION OF THE PREFERRED EMBODIMENTS

Figure 1:
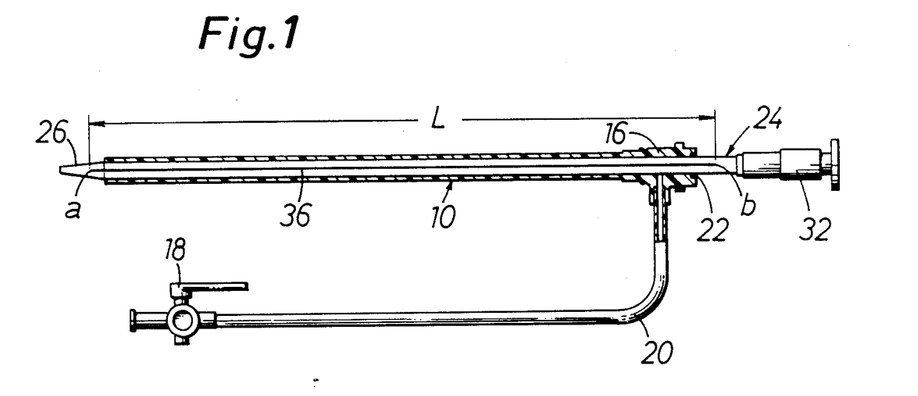
FIG. 1 is a side view, partly in section, showing the assembled state of a catheter introducer according to the invention.
Figure 2:
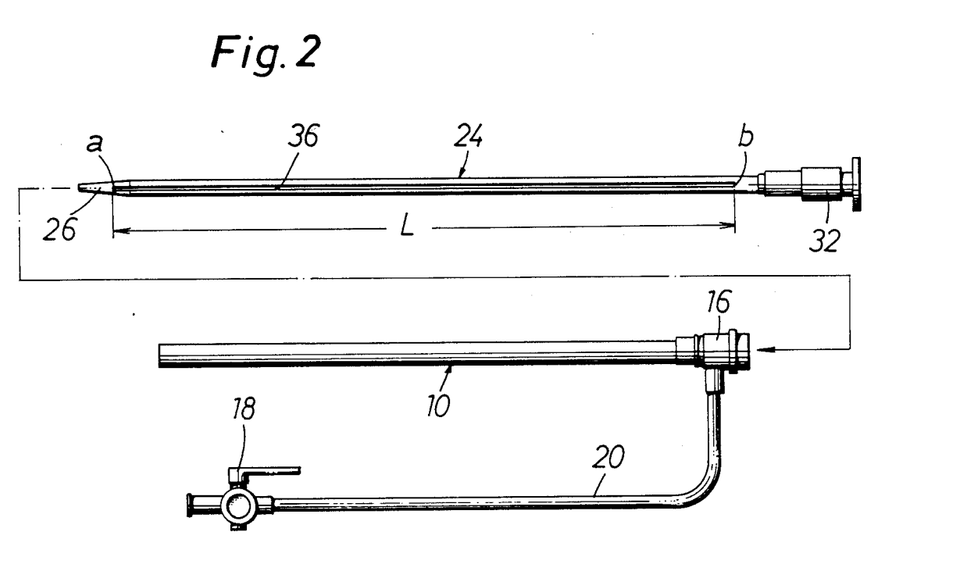
FIG. 2 is a side view showing the disassembled state of a sheath and a dilator.

The concrete construction of the invention will now be described in detail with reference to the drawings. In FIGS. 1 and 2 showing the assembled and disassembled states of a catheter introducer, the numeral 10 denotes a sheath for inserting a contrast medium injecting catheter 14 into a blood vessel 12, such as the brachial or femoral artery, said sheath being made from synthetic resin in the form of a hollow round pipe having a fixed length and a thickness as small as possible. The reference numeral 16 denotes a hollow hub continuously extending from the rear end of the sheath 10 and serving as a handle in use, said hub having communicatively connected thereto a transparent, medical liquid injecting tube 20 which is equipped with a valve 18, through which physiological saline containing heparin for preventing blood coagulation or some other medical liquid can be fed in. The numeral 22 denotes a diaphragm for preventing blood counterflow.

The numeral 24 denotes a dilator removably inserted through the inner hollow space of the sheath 10, said dilator being made from synthetic resin in the form of a relatively thick-walled hollow round pipe longer than said sheath 10. When it is extracted from the sheath 10, the counterflow preventive diaphragm 22 of said sheath 10 maintains the sealed state. The numeral 26 denotes a (forwardly descending) conical taper surface formed on the front end of the dilator 24; thus, the dilator can be easily inserted at its front end into a puncture hole 28 in a blood vessel 12 so that the puncture hole 28 can be smoothly dilated with the progress of insertion.

Figure 3:
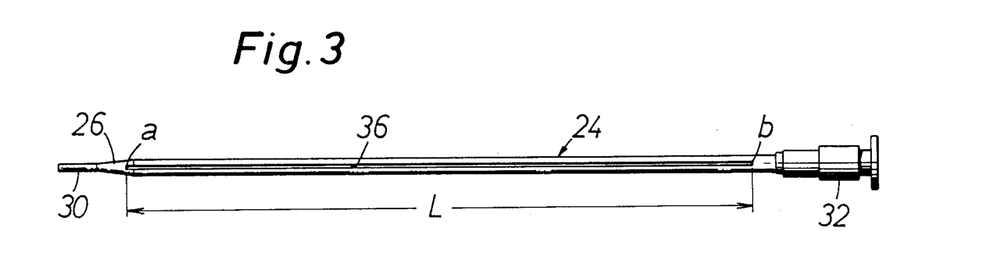
FIG. 3 is a side view showing a modification of a dilator alone.
Figure 4:
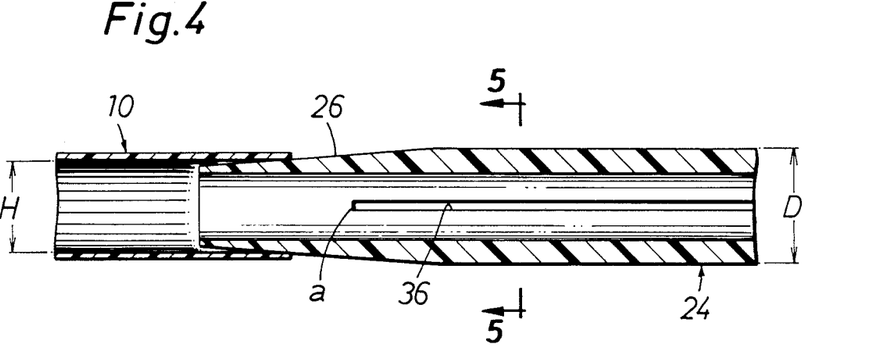
FIG. 4 is an enlarged fragmentary side view, in section, showing the start of insertion of the dilator into the sheath
Figure 5:
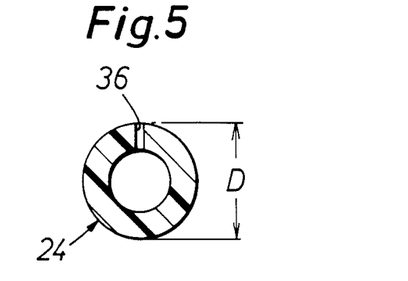
FIG. 5 is a sectional view taken along the line 5—5 in FIG. 4.
Figure 6:
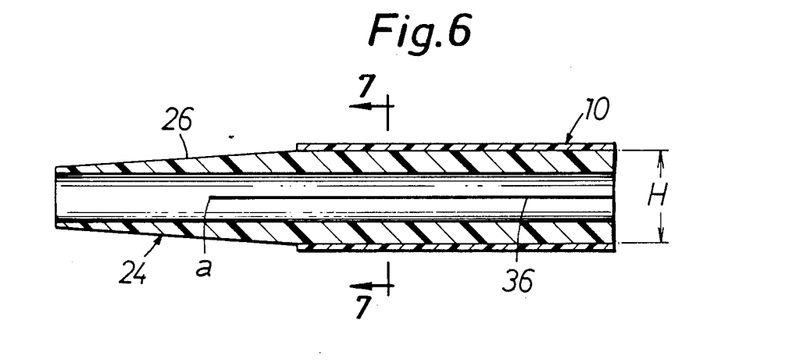
FIG. 6 is an enlarged fragmentary side view, in section, showing the completion of insertion of the dilator, corresponding to FIG. 4.
Figure 7:
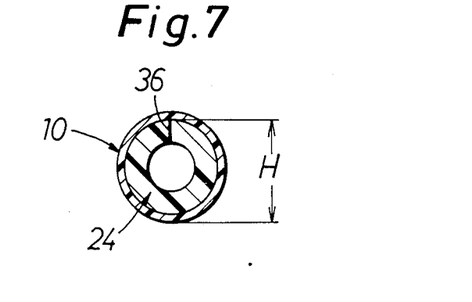
FIG. 7 is a sectional view taken along the line 7—7 in FIG. 6.

The forwardly descending conical taper surface 26, as shown in a modification in FIG. 3, may be positioned in the vicinity of the front end of the dilator 24, and located o the front end side is an insertion guide nose 30 in the form of a thin hollow straight pipe continuously extending therefrom. In either case, the rear end of said dilator 24 is diametrically bulged in the form of a slip-off preventing hub 32 which can be stably gripped in use.

· The dilator 24 is inserted on an introduction guide wire 34 for the catheter 14. That is, the inner diameter of the dilator 24 is smaller than the outer diameter of the cathete 14 and is larger than the outer diameter of the introduction guide wire 34.

In that case, in the present invention, as is clear from the enlarged views in FIGS. 4 through 7, the outer diameter D of the dilator 24 is made larger than the inner diameter H of the sheath 10, and the dilator 24 is formed with a slit 36 having a given length L and extending lengthwise thereof. The slit 36 is intended to produce a contractive elastic deformation action for changing the outer diameter D of the dilator 24, its opening front end a being positioned on said forwardly descending conical taper surface 26.

That is, when the dilator 24 is forcibly inserted at its front end into the hollow inner space of the sheath 10, the dilator 24 itself is contractively deformed through the closing action of the slit 36. Its subsequent automatic restoring elastic pressure for expansive deformation causes the dilator 24 to intimately contact the opening inner wall surface of the sheath 10. Since the opening front end a of the slit 36 is opposed to the forwardly descending conical taper surface 26 of the dilator 24, at the start of said insertion, the slit 36 is subjected to a gradual closing urging force from said conical taper surface 26, so that the dilator 24 smoothly contractively deforms of itself.

In FIGS. 1 and 2, except for the forwardly descending conical taper surface 26 at the front end and the hub 32, the outer diameter D of the whole of the dilator 24 is made larger than the outer diameter H of the sheath 10 and the long slit 36 is formed in the dilator substantially over its entire length, with the rear end opening b of said slit 36 being positioned in the vicinity of the hub 32. In a modification shown in FIGS. 8 and 9, only an intermediate portion of the dilator 24 may have its outer diameter D made somewhat larger than the inner diameter H of the sheath 10.

Figure 8:
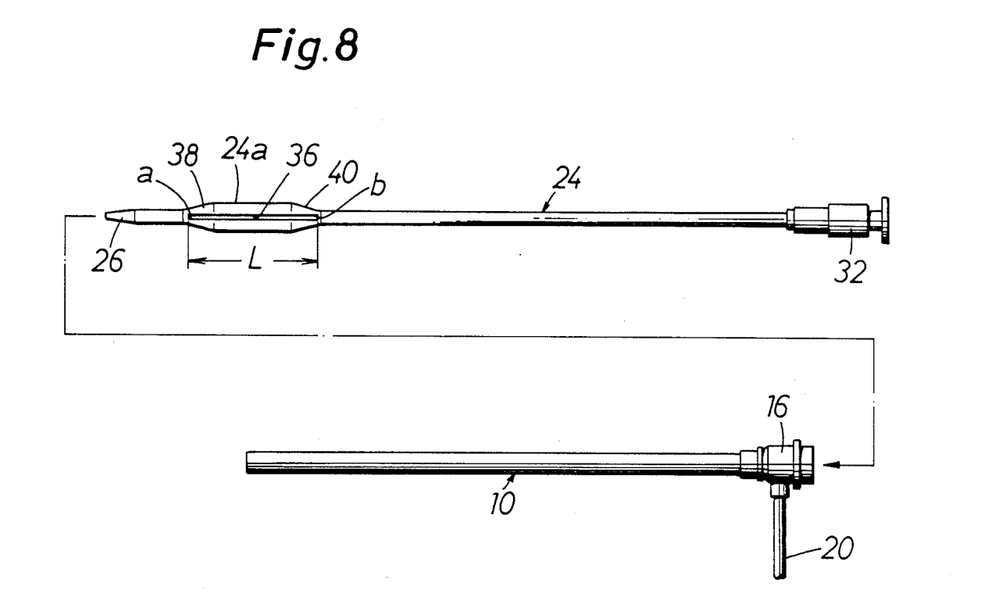
FIG. 8 is a side view showing the disassembled state of a dilator and a sheath according to another modification.
Figure 9:
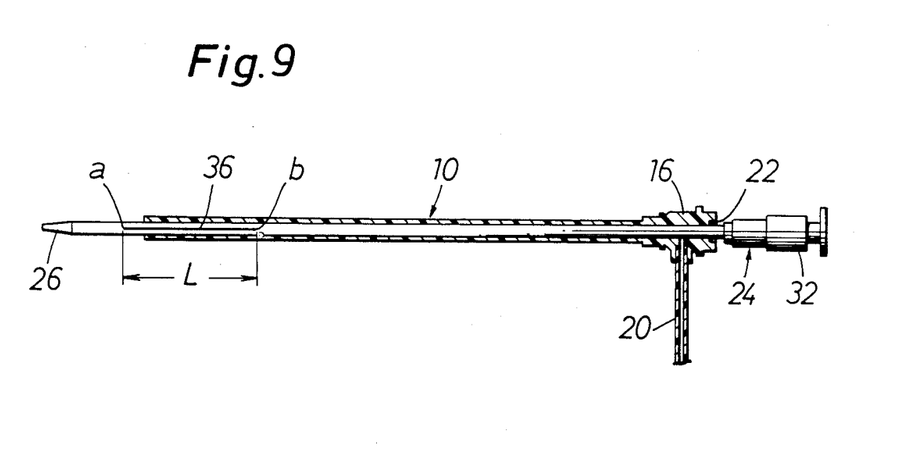
FIG. 9 is a fragmentary side view, partly in section, showing the assembled state of the introducer in FIG. 8

In this case, the thick portion 24a is smoothly connected to the remaining thin portion by means of a forwardly descending conical taper surface 38 and a rearwardly descending conical taper surface 40, and the given length L of the slit 36 is made shorter, with the opening front and rear ends a and b of said slit 36 being positioned on the forwardly and rearwardly descending conical taper surfaces 38 and 40, respectively.

With the arrangement thus made, when the dilator 24 is forcibly inserted through the hollow inner space of the sheath 10 in the same manner as described with reference to FIGS. 1 and 2, the dilator 24 itself contractively deforms through the closing action of the slit 36, as shown in FIG. 9, with its self-expanding restoring elastic pressure causing the dilator 24 to intimately contact the inner wall surface of the sheath 10. Therefore, such construction is included in the present invention.

On the basis of the catheter introducer of FIGS. 1 and 2, the method of use will now be described.

First, a puncturing needle (Seldinger needle) 46 comprising an assembly of an inner needle section 42 and an outer sleeve section 44, as shown in FIG. 10 (I), is used to form a puncture hole 28 in a blood vessel 12 such as the brachial or femoral artery. Then, the inner needle section 42 of the puncturing needle 46 is extracted while leaving the outer sleeve section 44 alone inserted held in the blood vessel 12. On the other hand, a relatively short catheter introducing guide wire 34 is inserted in advance in the dilator 24 in the catheter introducer which is in the assembled state.

Figure 10:
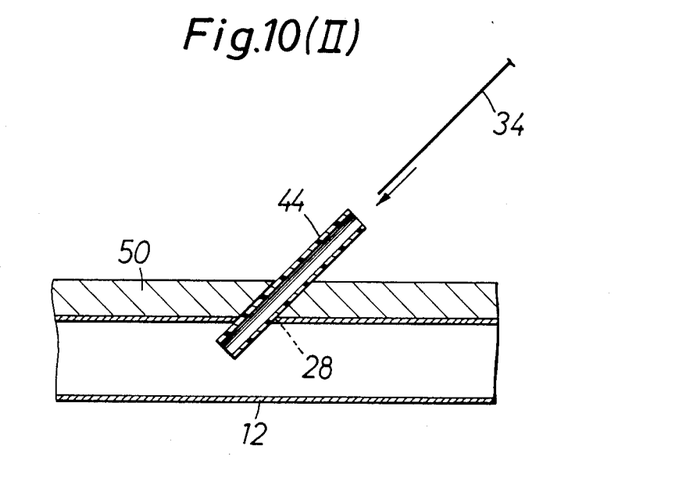
Figure 10I:
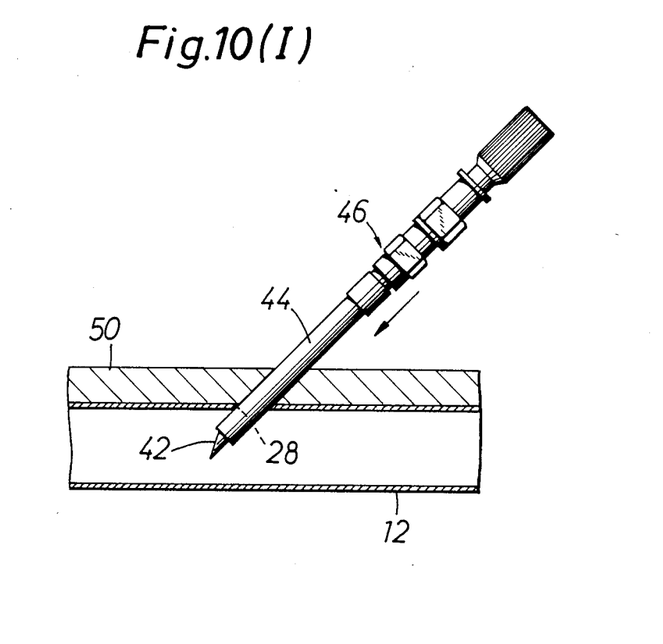

Then, through the outer sleeve 44 left behind as shown in FIG. 10 (II), the guide wire 34 is inserted into the blood vessel 12, whereupon the outer sleeve section 44 alone is extracted from the puncture hole 28 and, as shown in phantom lines in FIG. 10 (III), the outer sleeve 44 is split for removal.

That is, though not shown, the outer sleeve 44 is preferably one which is formed in advance with a tearing line or a weak portion for splitting purposes, so that such outer sleeve 44 can be extremely easily removed even from a longitudinal, intermediate position by splitting without having to extract the outer sleeve 44 from the guide wire 34.

Figure 10V:
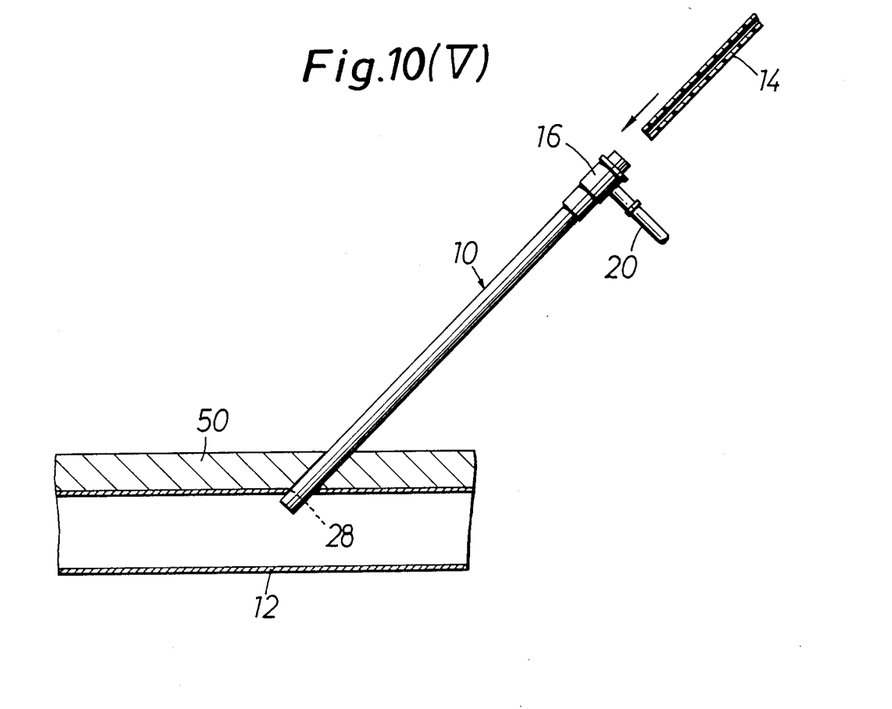

Then, as shown in the steps of FIGS. 10 (III) through 10 (IV), with the dilator 24 and the sheath 10 left in the assembled state, the catheter introducer is introduced from said puncture hole 28 along the guide wire 34 into the blood vessel 12 and then, with the sheath 10 alone left inserted as shown in FIG. 10 (V), the dilator 24 and the guide wire 34 are extracted.

On the basis of the guide action provided by the sheath left behind, as shown in FIG. 10 (VI), the catheter 14 is sent into the blood vessel 12. Finally, the sheath 10 is extracted and, as shown in FIG. 10 (VII), a contrast medium 48 is injected to conduct an angiographic test. In addition, the reference numeral 50 in FIG. 10 indicates subcutaneous tissue When said catheter 14 is to be used for selective or superselective insertion depending upon a primary, secondary or tertiary branch of the aorta, said catheter introducer and the short guide wire 34 are used as they are and the above-mentioned manipulation is repeated, whereby angiographic tests of the systemic arteries can be conducted in exactly the same way.

As has so far been described, the present invention provides a catheter introducer for angiography comprising a sheath 10 in the form of a hollow round pipe for inserting and guiding a catheter 14 into a puncture hole 28 in a blood vessel, and a dilator 24 in the form of a hollow round pipe removably inserted through said sheath 10 for receiving an introduction guide wire 34 for the catheter 14, said catheter introducer being characterized in that:

the outer diameter D of the dilator 24 is made larger than the inner diameter H of the sheath 10, while said dilator 24 is formed with a longitudinally extending slit 36 of given length L, so that the dilator 24 can be inserted through said sheath 10 while the dilator 24 is forcibly contractively deformed by the closing action of the slit 36, the contractive action being accompanied by a self-expansively deforming restoring elastic pressure which ensures that the dilator 24 intimately contacts the inner wall surface of the sheath 10. Thus, the invention has the effect of overcoming the problems of the prior art described at the outset.

Figure 11:
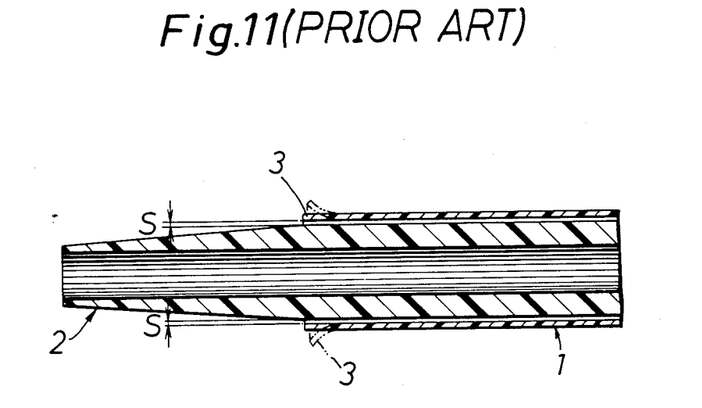
FIG. 11 is an enlarged fragmentary side view, in section, of a conventional catheter introducer.

That is, in a conventional catheter introducer, as shown in FIG. 11, the sheath 1 and the dilator 2 are maintained in a so-called double pipe type fitting state and constructed so that neither of their diameters produces a varying elastic action. Because of this construction, an air gap S produced in connection with manipulation for insertion and extraction and owing to dimensional errors produced during manufacture is inevitably present in the fitting surface.

As a result, even if the sheath 1 is reduced in wall thickness, the front end step portion 3 of the sheath 1 associated with the dilator 2 will later rub the opening edge of a puncture hole in a blood vessel, causing excessive direct stimulus or damage; the thinner the wall of the sheath 1, the more noticeable the phenomenon of the front end step portion 3 burring.

Figure 12:
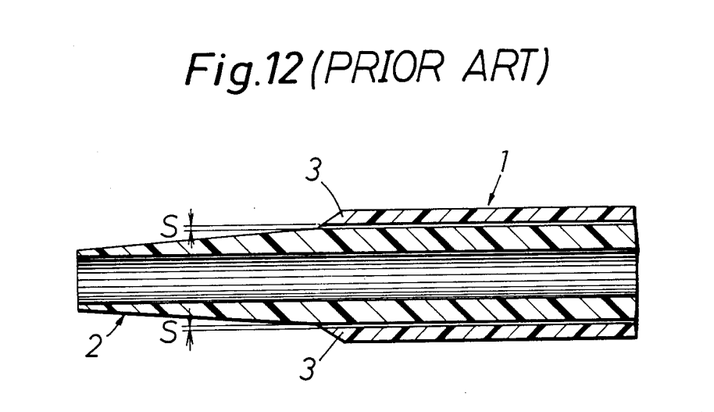
FIG. 12 is an enlarged fragmentary side view, in section, showing another conventional introducer.

To eliminate such burring phenomenon, as shown in FIG. 12, even if the sheath 1 is increased in wall thickness and made harder and the front end step portion 3 is formed with a forwardly descending, conical taper surface, the diameter of the sheath 1 becomes too large and the introducer itself becomes thicker, resulting in later expanding the puncture hole in the blood vessel, leading to another problem of difficulty in hemostasis.

According to the arrangement of the invention described above, these problems are all eliminated and the intended objects can be reliably attained. As for the necessary arrangement, it substantially suffices to simply form a slit 36 in the dilator 24; a mass-production effect can be expected to the greatest degree and the invention is very useful as a safe throwaway medical appliance.

I have conducted trans-brachial artery selective or superselective catheterization technique based on DSA directed to more than 300 patients. In remote-manipulating the catheter, I made it a rule to simultaneously use the introduction guide wire (trade name, Radiofocus M, described at the outset), whereby selective or superselective manipulation was possible with a probability of 98% with respect to systemic target arteries except the bronchial artery. In one case in early stages of this series of tests, an occlusion in the brachial artery was experienced as a side effect of the catheter manipulation, but by adding the aforesaid improvements to the catheter insertion technique and remote-manipulation technique, neither occlusion nor thrombus formation in the brachial artery occurred in the subsequent tests. Particularly, the catheter introducer of the present invention can be expected to enhance the safety of angiographic tests and to contribute to advancement of not only the trans-femoral but also the trans-brachial artery catheterization techniques.

While the invention has been particularly shown and described in reference to preferred embodiments thereof, it will be understood by those skilled in the art that changes in the form and details may be made therein without departing from the spirit and scope of the invention.

What is claimed is:

1. A catheter introducer for angiography, comprising: a sheath for inserting and guiding a catheter into a puncture hole in a blood vessel; and a dilator removably inserted through said sheath for receiving an introduction guide wire for the catheter, wherein the front end of said dilator being provided with a forwardly descending conical taper surface for smoothly expanding the puncture hole, wherein a rear end of said dilator being formed with a hub extending therefrom for preventing the slip-off of the sheath, wherein said sheath having a hollow hub extending from the rear end thereof, wherein said hub being connected for communication to a medical liquid injecting tube which is equipped with an on-off valve for injecting a solution selected from the group consisting of heparin-containing physiological saline solution and other medical liquids to prevent blood coagulation, wherein the outer diameter of a portion of said dilator subsequent to said forwardly descending taper surface is greater than the inner diameter of the sheath, wherein a slit for contracting said outer diameter is cut in said dilator to extend longitudinally along said dilator in the form of a line segment of a given length such that an opening front end of said dilator is positioned on the forwardly descending taper surface and an opening rear end of said dilator is limited from reaching a sheath slip-off preventing hub of said dilator, and wherein said dilator being inserted through the sheath while being forcibly contracted to cause said slit to close, and wherein the dilator is intimately contacted with the inner wall surface of the sheath.

2. A catheter introducer for angiography as set forth in claim 1, wherein the outer diameter of the dilator is increased at an intermediate portion thereof so that it is greater than the inner diameter of the sheath.

3. A catheter introducer for angiography as set forth in claim 1, wherein the dilator is formed with a forwardly descending conical taper surface and the opening front end of the slit is positioned on said conical taper surface.

* * * * *